(12) United States Patent
Zhang

(10) Patent No.: US 6,544,270 B1
(45) Date of Patent: Apr. 8, 2003

(54) MULTI-LUMEN CARDIAC CATHETER AND SYSTEM

(75) Inventor: Yongxing Zhang, Little Canada, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 9 days.

(21) Appl. No.: 09/661,928

(22) Filed: Sep. 14, 2000

(51) Int. Cl.⁷ .................................................. A61N 1/05
(52) U.S. Cl. .................... 606/129; 604/43; 604/264; 607/122
(58) Field of Search ................. 604/35, 43, 164.05, 604/164.06, 264–266; 600/372–374, 377, 505; 607/115, 116, 119, 122, 123; 606/108, 129

(56) References Cited

U.S. PATENT DOCUMENTS

| | | | | |
|---|---|---|---|---|
| 4,447,239 A | * | 5/1984 | Krutten | 604/529 |
| 4,917,104 A | | 4/1990 | Rebell | 128/772 |
| 5,167,623 A | * | 12/1992 | Cianci et al. | 604/43 |
| 5,209,229 A | | 5/1993 | Gilli | 128/419 D |
| 5,221,255 A | | 6/1993 | Mahurkar et al. | 604/43 |
| 5,243,976 A | | 9/1993 | Ferek-Pertric et al. | 607/6 |
| 5,246,014 A | | 9/1993 | Williams et al. | 607/122 |
| 5,255,691 A | | 10/1993 | Otten | 607/117 |
| 5,316,001 A | | 5/1994 | Ferek-Petric et al. | 128/661.08 |
| 5,374,245 A | | 12/1994 | Mahurkar | 604/43 |
| 5,423,806 A | | 6/1995 | Dale et al. | 606/15 |
| 5,607,462 A | * | 3/1997 | Imran | 607/122 |
| 5,632,749 A | | 5/1997 | Goode et al. | 606/108 |
| 5,674,217 A | | 10/1997 | Wahlstrom et al. | 606/15 |
| 5,697,936 A | | 12/1997 | Shipko et al. | 606/108 |
| 5,755,766 A | | 5/1998 | Chastain et al. | 607/122 |
| 5,769,858 A | | 6/1998 | Pearson et al. | 606/108 |
| 5,803,928 A | | 9/1998 | Tockman et al. | 607/122 |
| 5,879,499 A | | 3/1999 | Corvi | 156/175 |
| 5,902,331 A | | 5/1999 | Bonner et al. | 607/122 |
| 5,908,447 A | | 6/1999 | Schroeppel et al. | 607/126 |
| 5,957,966 A | | 9/1999 | Schroeppel et al. | 607/122 |
| 5,980,478 A | * | 11/1999 | Gorsuch et al. | 604/408 |
| 6,002,969 A | | 12/1999 | Machek et al. | 607/122 |
| 6,024,764 A | | 2/2000 | Schroeppel | 623/1 |
| 6,083,216 A | | 7/2000 | Fischer, Sr. | 604/530 |
| 6,132,456 A | | 10/2000 | Sommer et al. | 607/127 |
| 6,136,005 A | | 10/2000 | Goode et al. | 606/108 |

* cited by examiner

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

A system which includes a catheter and at least a first and second lead, where the catheter includes an elongate catheter body having at least two lumens through which the first and second leads pass. In one embodiment, the leads are reduced diameter leads having a complete, partial or no stylet lumen. The elongate catheter body further includes a first section and a second section, where there is a transition (e.g., a tapered portion) between the first section and the second section. A first lumen extends through the first section and the second section between a first inlet at the proximal end to a first outlet at the distal end. A second lumen extends through the first section between a second inlet at the proximal end to a second outlet at a point in the first section. In one embodiment, the second outlet is located approximately at the transition between the first section and the second section.

36 Claims, 12 Drawing Sheets

MULTI-LUMEN CARDIAC CATHETER AND SYSTEM

FIELD OF THE INVENTION

The present invention relates generally to catheters, and more particularly to cardiac catheters having multiple lumens.

BACKGROUND

Implantable leads form an electrical connection between a pulse generator or other electronic device and a tissue or structure in the body. For example, leads transmit electric signals in one direction to stimulate cardiac tissue and in the opposite direction sensed from the cardiac tissue. To sense signals, leads typically include one or more electrical elements positioned on the lead. These electrical elements are typically referred to as electrodes and they are adapted to sense cardiac signals and to provide electrical energy to the cardiac tissue. Leads also typically include a lead connector pin at the lead's proximal end. Lead connector pins are adapted to electrically and mechanically connect leads to the pulse generator or other electronic medical device. A flexible conductor electrically couples the electrode to the lead connector pin. Commonly, the flexible conductor takes the form of a single or multifilar wire coil. The flexible conductors are then surrounded by a layer of insulating material that together form what is referred to as the lead body. The lead body couples the lead connector pin at the proximal end with the electrodes at the distal end.

Cardiac pacemakers for treating bradycardia commonly employ pacing leads for connecting an electrical impulse generator to an excitable cardiac tissue, usually within the heart's right ventricle. Researchers have found that cardiac stimulation can also be beneficial in treating patients suffering from congestive heart failure (CHF). By properly controlling the interval between the atrial contraction and the ventricular contraction (i.e., the AV interval) with the pacemaker, a heart may be induced to pump more efficiently. Pacing therapy for the treatment of CHF, however, often requires the ability to stimulate the left ventricle, either alone or in conjunction with right ventricle. One way of providing stimulation to the left ventricle is through the use of a left ventricular access (LVA) leads. This type of lead is introduced through the coronary sinus vein and advanced through the cardiac veins so as to position the one or more electrodes on the lead on the cardiac tissue adjacent the left ventricle.

The introduction of a lead into the cardiovascular system partially obstructs blood flow. This is especially true when the cardiac lead is implanted into the coronary veins, where placement of a lead into the coronary veins may exacerbate an individual's cardiac condition. The size of the lead is also a concern when they are used in children. Children are inherently more susceptible to having blood flow obstructed because many of their blood vessels are simply too small to accommodate conventional implantable leads. As a result, these adult patients may not be suitable candidates for transvenous implanted leads because of the diameter of currently available leads.

Conventional lead bodies have an internal lumen that is coextensive with the lead body. The lumen is adapted to receive a stylet, where the stylet is used to push and steer the lead through the vessels to a target location within the heart. The lumen, however, constitutes a significant portion of the overall diameter of the lead body. Therefore, a trade-off of lead body diameter is made for the ability to utilize a stylet while implanting the cardiac lead. What is needed, however, is an apparatus, system and method which can allow for leads having lead bodies of reduced size to be implanted into the heart, including the cardiac veins.

SUMMARY

The present subject matter provides an apparatus, system and method which addresses the need for handling and delivering cardiac leads having lead bodies of reduced size. In reducing the size of the cardiac lead, support and guidance structure is typically removed. The present subject matter provides the reduced size cardiac leads with support and guidance during the time that such support and guidance is needed, during implant. Once the leads have been implanted, the support and guidance structures that would typically have been left in the vasculature only to unnecessarily occlude the vasculature is removed. Thus, the present apparatus, system and method provide an important advancement in the delivery and placement of reduced size cardiac leads.

In one embodiment, there is provided a system having catheter and at least a first cardiac lead and a second cardiac lead. The catheter includes an elongate catheter body with at least two lumens, where each of the lumens is adapted to pass a cardiac lead. The elongate catheter body includes a first section and a second section. In one embodiment, the elongate catheter body has a tapered transition between the first section and the second section. A first lumen extends through the first section and the second section between a first inlet at the proximal end to a first outlet at the distal end. A second lumen extends through the first section between a second inlet at the proximal end to a second outlet in the first section. In one embodiment, the second outlet is located in the tapered region. The first cardiac lead is located at least partially in and passes through the first lumen of the elongate catheter body. The second cardiac lead is located in and at least partially in and passes through the second lumen of the elongate catheter body.

In positioning the leads in the heart, the catheter is first positioned at least partially within the heart. In one embodiment, a guidewire is first inserted into the heart. The catheter is positioned over the guidewire and then inserted into the heart. The guidewire is then removed from the heart and the cardiac leads are inserted into the lumens of the catheter. One the cardiac leads are implanted into the desired location within the heart, the elongate catheter is removed from the heart. In an alternative embodiment, the catheter is positioned at least partially within the heart without the use of a guidewire.

In order to allow the leads to pass more easily through the lumens, the walls of the lumens are coated with a lubricant. In an additional embodiment, the catheter body is made radiopaque to allow for the catheter to be visualized within the vasculature and heart. In an additional embodiment, the catheter body is splitable to allow the catheter to be more easily passed around the implanted leads and to removed the catheter from the patient. In one embodiment, the catheter body separate into two or more pieces to allow the catheter to be passed around the leads. The splitable catheter body includes two or more segments, where the segments are defined by sections of the catheter body that are weaker relative to the remainder of the catheter body, where the two or more segments are adapted to separate from each other along the sections. In one embodiment, the sections along the catheter body are slits which extend longitudinally along the catheter body.

These and other embodiments, aspects, advantages, and features will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Cardiac lead design has begun to focus on producing lead bodies having smaller and smaller diameters. This allows the cardiac leads to be positioned in more locations throughout the heart, including in positions deep within the coronary veins. For example, a small diameter cardiac leads is placed adjacent the left atrium and/or ventricle by inserting the cardiac lead through the coronary sinus, through the great cardiac vein and into any number of tributary veins to allow for one or more electrodes on the lead to be positioned adjacent the left atrium and/or ventricle. Alternatively, more than one cardiac lead is inserted into the coronary veins to allow for cardiac signals to be sensed from and pulses to be delivered to more then one location within the coronary veins. The smaller diameter lead bodies also allow for less area to be occluded within the vessel and for a more flexible lead. The greater flexibility provides for less interference with the operation of the heart.

As the cardiac lead diameters become smaller and smaller, ways of delivering the leads become more difficult. Simply inserting the cardiac lead without use of a device to control the lead would be ineffective due to the highly flexible characteristic of the lead. Typically, the travel of the lead through the vasculature and into the heart is controlled through the use of a stylet. The stylet is a flexible wire which is inserted into the lead body and provides a means of pushing and steering the lead through the vasculature and into the heart. However, having the stylet lumen necessarily increases the diameter of the lead as compared to a lead without the lumen. The present subject matter allows for one or more cardiac leads either with reduced diameter stylet lumens, partial stylet lumens or without a stylet lumen to be guided through the vasculature and inserted into the heart.

Figure 1:
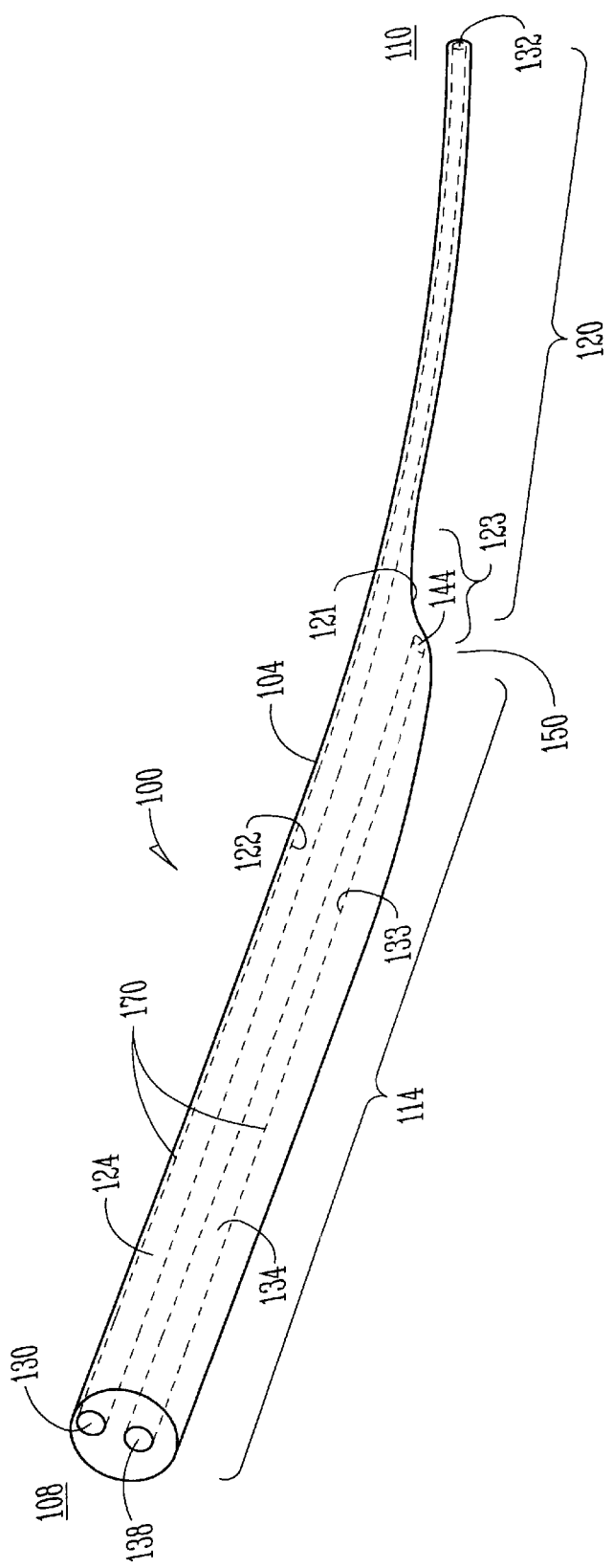
FIG. 1 shows a perspective view of an exemplary embodiment of a catheter.

FIG. 1 is one exemplary embodiment of a catheter 100. The catheter 100 includes an elongate catheter body 104 having a proximal end 108 and a distal end 10. The elongate catheter body 104 includes a first section 114 and a second section 120, where there is a transition 121 in the cross-sectional shape of the catheter body 104 between the first and second sections 114 and 120. In one embodiment, the transition 121 is a taper 123 having a circular cross-sectional shape from the first section 114 to the second section 120. The elongate catheter body 104 also includes a first wall 122 which defines a first lumen 124. The first lumen extends through the first section 114 and the second section 120. The first lumen 124 further includes a first inlet 130 at the proximal end 108 and a first outlet 132 at the distal end 110, where the first lumen 124 is adapted to receive and pass a cardiac lead.

The elongate catheter body 104 further includes a second wall 133 which defines a second lumen 134. The second lumen 134 extends through the first section 114 between a second inlet 138 at the proximal end 108 to a second outlet 144 in the first section. In one embodiment, second outlet 144 is located between the proximal end 108 and the distal end 110. As with the first lumen 124, the second lumen 134 is also adapted to receive and pass a cardiac lead.

The first lumen 124 and the second lumen 134 each have a longitudinal axis which is separated from and parallel to each other, so that each lumen is spaced apart and separated from each other by the elongate catheter body 104 (i.e., the elongate catheter body 104 defines and separates each lumen). In one embodiment, the longitudinal axis of the first lumen 124 and the second lumen 134 are eccentric with respect to each other (i.e., the longitudinal axis of the first lumen 124 and the second lumen 134 do not have a common center with respect to each other). The first lumen 124 also has a first lumen length that is greater than a second lumen length of the second lumen 134. In one embodiment, the second lumen length of the second lumen 134 is approximately the length of the first section 114. In one embodiment, the catheter 100 has a length of 30 to 50 centimeters, where, by way of example only, the first section 114 has a length of approximately 25 to 50 centimeters, and the second section 120 has a length of approximately 6 to 15 centimeters.

In the exemplary embodiment of FIG. 1 there is shown a change in the diameter of the catheter body 104 at approximately 150. In one embodiment, the change in the catheter body 104 is a tapered region 123 which makes the transition 121 between the first section 114 and the second section 120 of the catheter body 104. The second outlet 144 is located on the catheter body 104 along the tapered region 123. The transition 121 also provides the second section 120 with a smaller profile than the first section 114. This in turn allow the second section 120 to be inserted into areas which would not accommodate the first section 114.

The first lumen 124 and the second lumen 134 are both adapted to receive and pass a cardiac lead. In one embodiment, the first lumen 124 has a first lumen diameter and the second lumen 134 has a second lumen diameter that is of a size that is sufficient to receive and pass a cardiac lead (i.e., to allow the cardiac lead to move completely through the lumen). In one embodiment, lumens are adapted to receive and pass cardiac leads having diameters in the range of approximately 0.5 millimeters to 2 millimeters.

In one embodiment, the catheter body 104 is constructed of an extruded thermopolymer. For example, the catheter body 104 is constructed of polyetheramide or any number of biocompatable polymers or co-polymers. In addition, the first wall 122 and/or the second wall 133 of the catheter body 104 optionally include a lubricious coating 170, which reduces the coefficient of friction between the cardiac lead and the catheter body 104. In one embodiment, the lubricous coating 170 is, for example, a hydrogel, cross-linked silicon, or other biocompatible lubricious coating materials applied by various means and manufacturing processes. In an additional embodiment, the catheter body 104 is made radiopaque. One reason for making the catheter body 104 radiopaque is to allow for the catheter 100 to be visualized as it is inserted into the patient.

Figure 2:
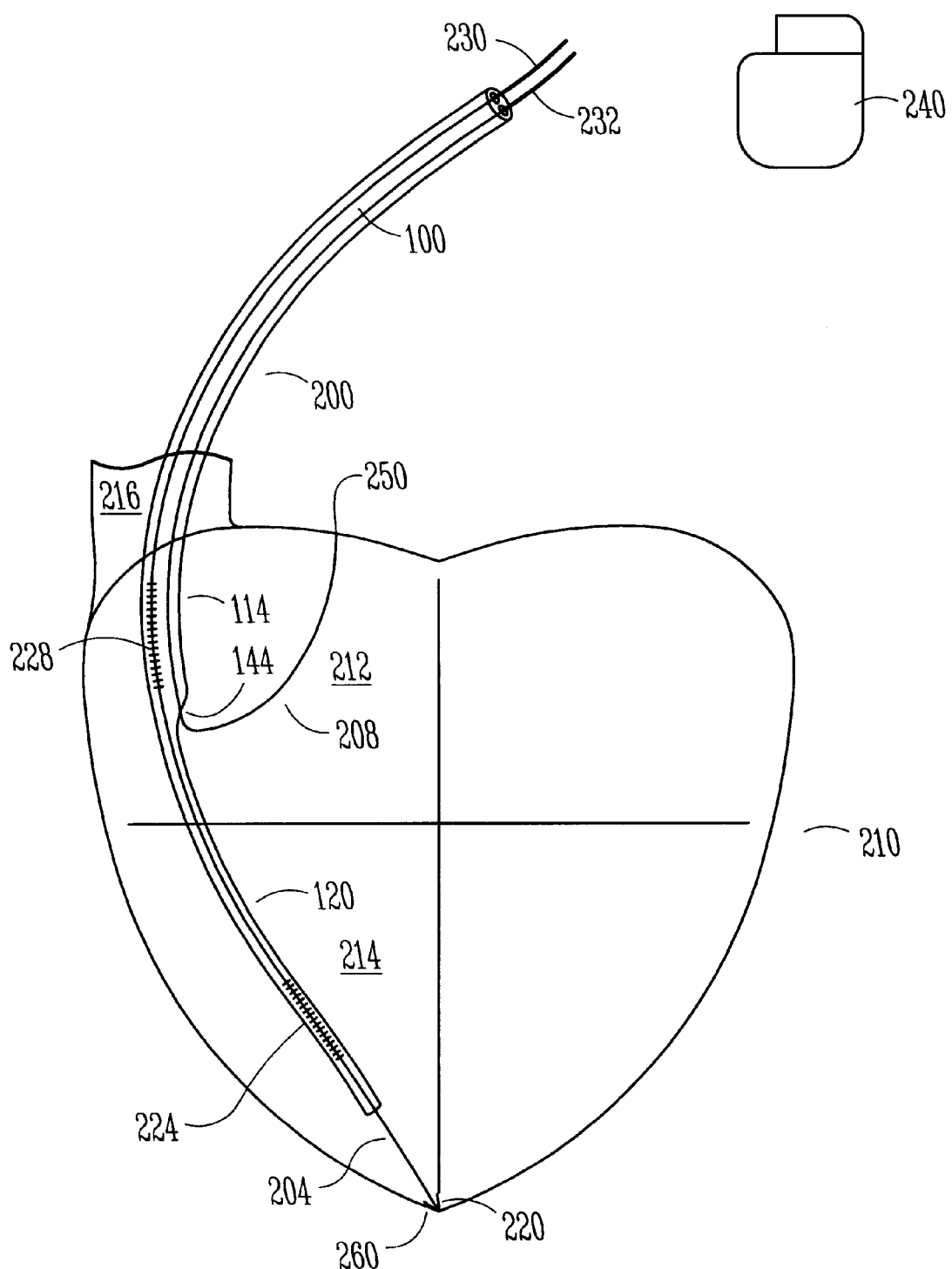
FIG. 2 shows a view of an exemplary embodiment of a system partially implanted in a heart from which segments have been removed to show detail.

FIG. 2 shows an exemplary embodiment of a system 200. The system 200 includes the catheter 100 as previously described, along with a first cardiac lead 204 and a second cardiac lead 208. The system 200 is shown in one example, positioned in a heart 210, with the second section 120 positioned partially in the right atrium 212 and partially the right ventricle 214 of the heart 210, and the first section 114 positioned partially in the right atrium 212 and partially in the superior vena cava 216.

In an alternative embodiment, the first section 114 and the second section 120 of the catheter 100 are positioned in alternative locations within the heart to allow for the first and second cardiac leads 204 and 208 to be delivered to different areas of the heart 210. For example, both the first section 114 and the second section 120 are positioned in the supraventricular region of the heart. In one embodiment, the first section 114 is positioned in at least a portion of the superior vena cava 216 and the right atrium 212 and the second section 120 is positioned within one or more of the coronary veins. From this position, the first cardiac lead 204 is delivered within the coronary veins to a supraventricular and/or ventricular location and the second cardiac lead 208 is positioned within either a right atrium 212 or adjacent a right ventricular 214 position.

In the exemplary embodiment of FIG. 2, the first lead 204 is shown positioned within the first lumen 124, where the first cardiac lead 204 passes through the first lumen 124 of the elongate catheter body 104. Similarly, the second lead 208 is shown positioned at least partially within the second lumen 134, where the second cardiac lead 208 passes through the second lumen 134 of the elongate catheter body 104.

Figure 3:
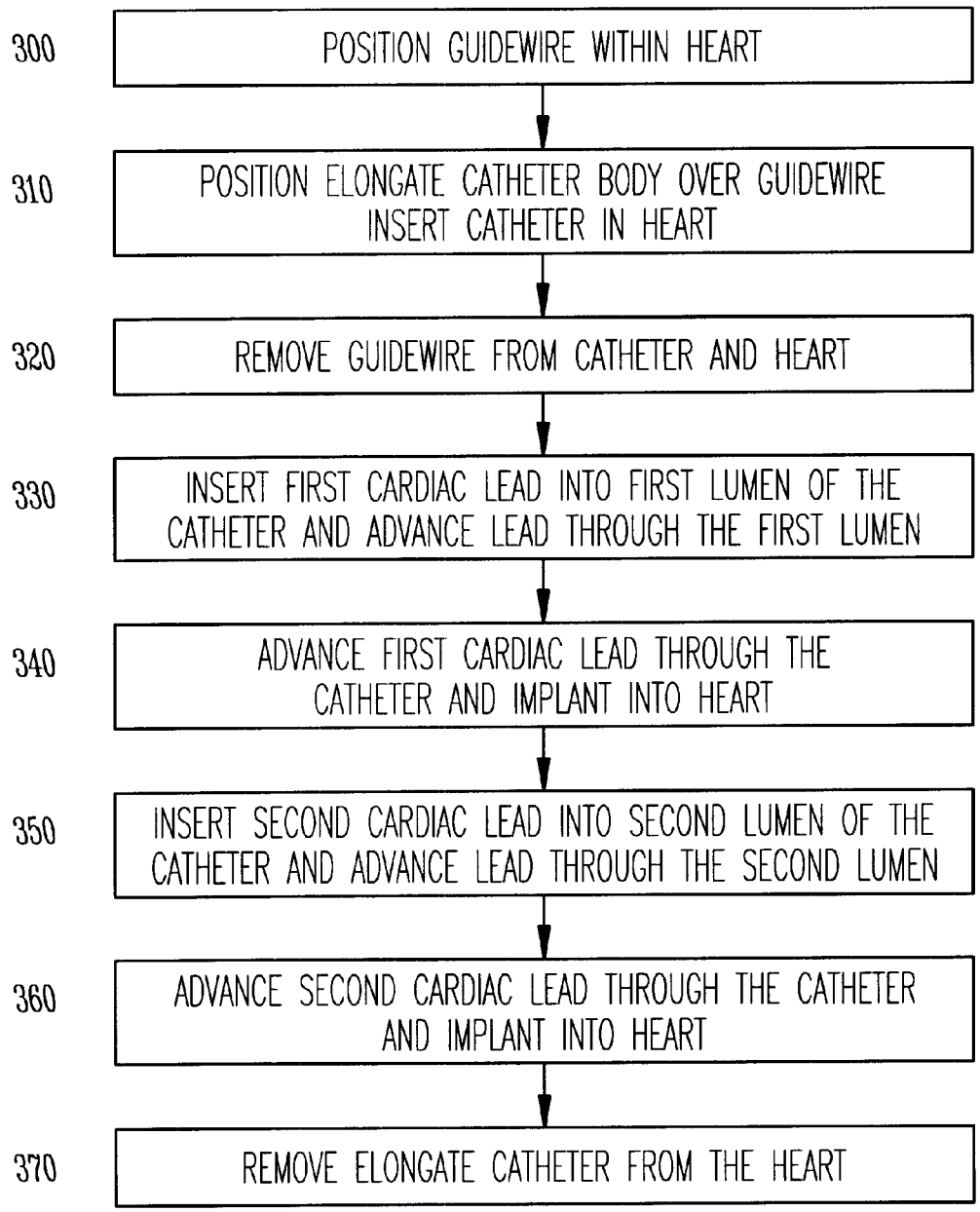
FIG. 3 shows an exemplary embodiment of a method for the system.

FIG. 3 shows an exemplary embodiment of a method of positioning the catheter and the leads. At 300, a guidewire is first positioned within a heart. In one embodiment, the guidewire is introduced into the venous system, for example through the subclavian vein or cephalic vein, and guided into position within the heart. In one embodiment, the distal end of the guidewire is located where the distal end of the catheter is to be positioned. So, for example, when the distal end of the catheter is to be positioned in the right ventricle, the distal end of the guidewire is first positioned in the right ventricle. Once the guidewire is positioned within the heart, the elongate catheter is then positioned over the guidewire and the catheter is inserted into the heart at 310. In one embodiment, the guidewire is inserted into a lumen, such as the first lumen 124 or the second lumen 134 of the catheter 100 and the catheter is moved through the vasculature as the catheter slides over the guidewire.

The catheter is slid over the guidewire until the distal end of the catheter is positioned at the desired location within the heart, with the proximal end of the catheter positioned outside of the body. In one embodiment, the length of the first and second sections 114 and 120 will depend in part upon one or more of the size of the patient, the entry point for the catheter and the desired location of the outlets for the catheter. In one embodiment, the elongate catheter being inserted into the heart is visualized and positioned through the use of a venogram. Once the catheter is positioned within the heart, the guidewire is removed from the catheter and the heart at 320. In an alternative embodiment, the catheter is positioned at least partially within the heart without the use of a guidewire, where the catheter body has sufficient stiffness and pushability to allow the catheter to be advanced through the vasculature to the desired location.

At 330, the first cardiac lead is inserted into the first lumen of the catheter and the first cardiac lead is advanced through the first lumen. In one embodiment, the lumen wall of the catheter is sufficiently stiff to provide support to the cardiac lead such that the pushing force on the cardiac lead translates into the lead being advanced (i.e., moved) through the lumen. In an alternative embodiment, the first cardiac lead is advanced through the first lumen of the elongate catheter through the use of a stylet.

The first cardiac lead is advanced through the catheter and implanted into the heart at 340. In one embodiment, the distal end of the catheter is positioned adjacent the location where the distal end of the first cardiac lead is to be implanted. The first cardiac lead is then advanced through the catheter lumen until the distal end of the lead emerges from the catheter. This allows for a minimal amount of the cardiac lead to extend beyond the outlet of the lumen so that the column strength of the lead is still sufficient to allow for it to be advanced against and secured to the endocardial tissue. Alternatively, the distal end of the catheter is positioned generally in the area of the heart into which the cardiac lead is to be implanted. The cardiac lead is then advanced through the lumen and into the heart. In one embodiment, this latter embodiment is utilized where the cardiac lead is not actively fixed (i.e.,screw-in type lead) to the cardiac tissue.

Referring again to FIG. 2, the first lead 204 includes tines 260 at or adjacent the distal end of the lead 204 to allow for passive fixation to the cardiac tissue. Alternatively, the first lead 204 includes an active fixation device to engage the cardiac tissue, such as a distal tip "screw-in" type electrode or barbed tip electrodes, or annular or semi-annular electrodes mounted on the lead body that have one or more fixation devices associated with them. In one embodiment, the lead body is sufficiently stiff to transfer the torque required to engage the active fixation electrode into the cardiac tissue.

The first cardiac lead is implanted through the catheter into any number of locations within the heart. For example, the first cardiac lead is implanted in either a supraventricular or a right ventricular location. In one embodiment, implanting the first cardiac lead includes implanting the first cardiac lead into a right ventricle of the heart. Alternatively, implanting the first cardiac lead includes implanting the first cardiac lead into a right atrium of the heart. Implanting the first cardiac lead in other locations within the heart and/or vasculature is also possible, from where cardiac signals are sensed and electrical energy pulses are delivered.

Referring again to FIG. 3, the second cardiac lead is then inserted into the second lumen of the catheter and the second cardiac lead is advanced through the second lumen at 350. In one embodiment, the lumen wall of the catheter is sufficiently stiff to provide support to the cardiac lead such that the pushing force on the cardiac lead translates into the lead being advanced (i.e., moved) through the lumen. In an alternative embodiment, the second cardiac lead is advanced through the second lumen of the elongate catheter through the use of a stylet.

The second cardiac lead is advanced through the catheter and implanted into the heart at 360. In one embodiment, the second outlet of the catheter is positioned in the region of the heart where the second cardiac lead is to be implanted. For example, when the second lead is to be implanted in a supraventricular region of the heart (e.g., right atrium, or adjacent the left atrium), the second outlet of the catheter is positioned generally in the chamber of the right atrium. One example of this is shown in FIG. 2.

Figure 4:
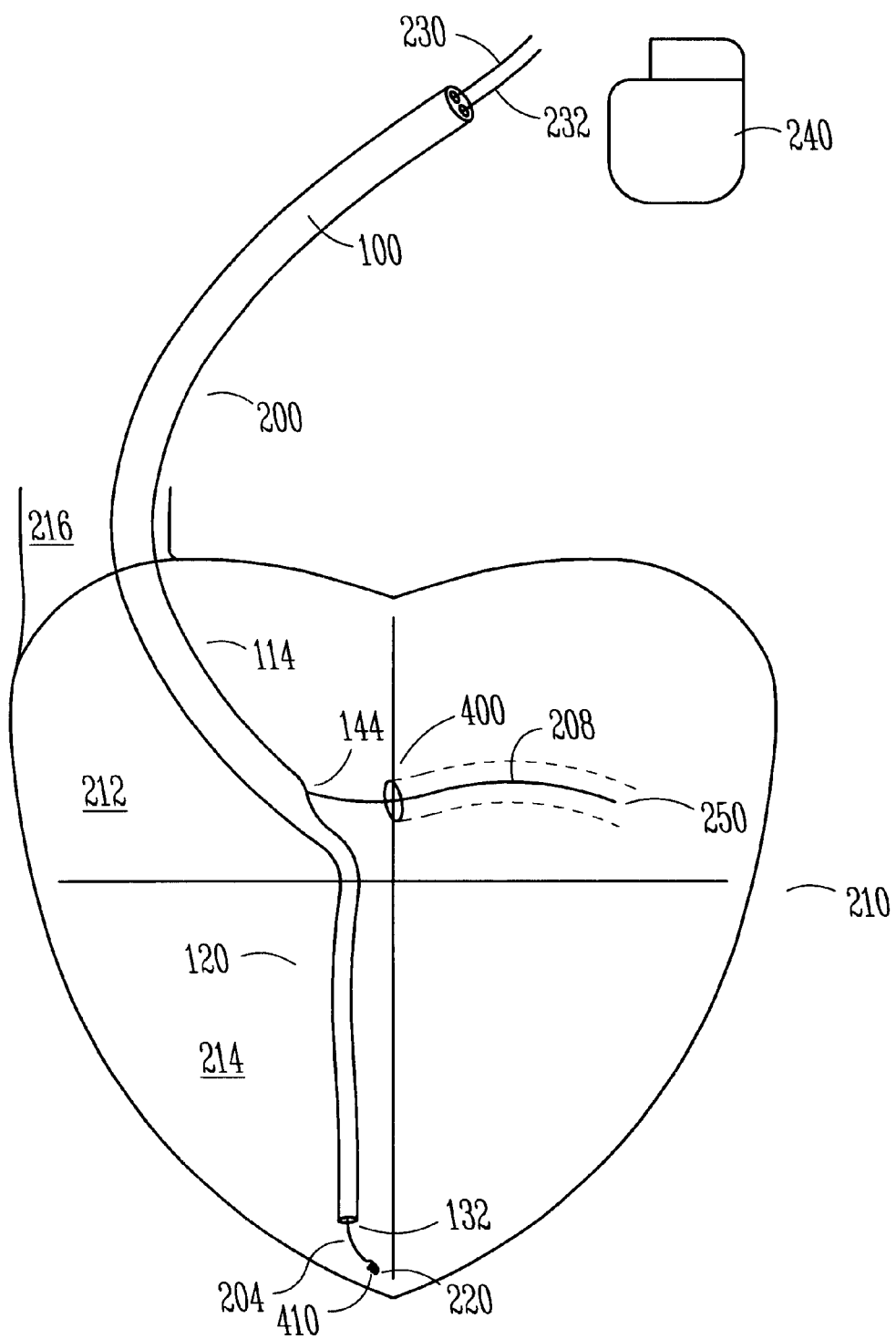
FIG. 4 shows a view of an exemplary embodiment of a system partially implanted in a heart from which segments have been removed to show detail.

FIG. 4 shows an alternative embodiment of system 200 positioned in the heart 210, with the second outlet 144 positioned in the right atrium 212 adjacent the outlet of the coronary sinus vein 400. Positioning the second outlet 114 adjacent the coronary sinus 400 allows the second lead 208 to be inserted into the coronary sinus vein and positioned adjacent the left atrium and/or left ventricle via the coronary veins. In one embodiment, the second lead is either passively secured to the cardiac chamber and/or within the coronary vein (e.g., through the use of tines on the lead body or bends or deflections imparted into the lead body), or is actively fixed to the cardiac tissue with one or more active fixation devices. Such devices include distal tip "screw-in" type electrodes or barbed tip electrodes, or annular or semi-annular electrodes mounted on the lead body that have one or more fixation devices associated with them. FIG. 4 also shows the embodiment where the distal end of the first lead 204 includes an active fixation device 410 to engage the cardiac tissue of the heart 210. In the embodiment of FIG. 4, the active fixation device 410 is a distal tip "screw-in" type electrode or barbed tip electrodes. In one embodiment, the lead body for either the first or second leads 204 or 208 is sufficiently stiff to transfer the torque required to engage the active fixation electrode into the cardiac tissue.

Referring again to FIG. 2, the leads 204 and 208 include any number and combination of pacing and/or defibrillation electrodes. For example, the first lead 204 includes a pace/sense electrode 220 located at or adjacent to the distal end of the first lead 204. The first lead 204 also includes a first defibrillation electrode 224 and a second defibrillation electrode 228 (shown in outline within the catheter 100). In one embodiment, the first and second defibrillation electrodes 224 and 228 are positioned along the first lead 204 so that when the pace/sense electrode 220 is positioned in the apex of the right ventricle 214 the first defibrillation electrode 224 is within the right ventricle 214 and the second defibrillation electrode 228 is positioned at least partially with in the right atrium 212 of the heart 210. The leads 204 and 208 further include connectors 230 and 232, respectively, which allow for the leads to be physically and electrically coupled to an implantable pulse generator 240. The electrodes on the first lead 204 are used to sense one or more cardiac signals and deliver pulses of electrical energy to the heart through the electrodes.

Additionally, the second lead 208 optionally includes one or more pace/sense electrodes and/or one or more defibrillation electrodes. For example, in FIG. 2 the second lead 208 is shown with a first pace/sense electrode 250 at or adjacent the distal end of the lead body. From the first pace/sense electrode 250 a cardiac signal is sensed and pulses of electrical energy are delivered to the supraventricular location of the heart 210. Additionally, the second lead 208 has any number pre-cast shapes to allow the lead to be place in and conform to the anatomical structures of the heart. For example, the second lead 208 has a "J" curve at the distal portion of the lead to allow the lead to make contact with the endocardial wall of the right atrium. Furthermore, any of leads in the present subject matter has a preformed shape (either imparted when the lead is cast or extruded or imparted by the shape of the conductor wire within the lead body), including, but not limited to, helical, zig-zag, one or more lateral deflections, and other bias shapes and designs. In one embodiment, the leads are made of biocompatable polymers, such as polyurethanes or silicones.

As previously stated, the reduced size leads used in conjunction with the catheter either includes a complete full lead length stylet lumen, a partial lead length lumen or no stylet lumen. When a partial lead length stylet lumen or no stylet lumen are included, a pushing stylet is used to advance the lead through the catheter lumen, where the pushing stylet engages at least a portion of the lead near the distal end of the lead to allow for the lead to be advanced through the catheter lumen.

Figure 5:
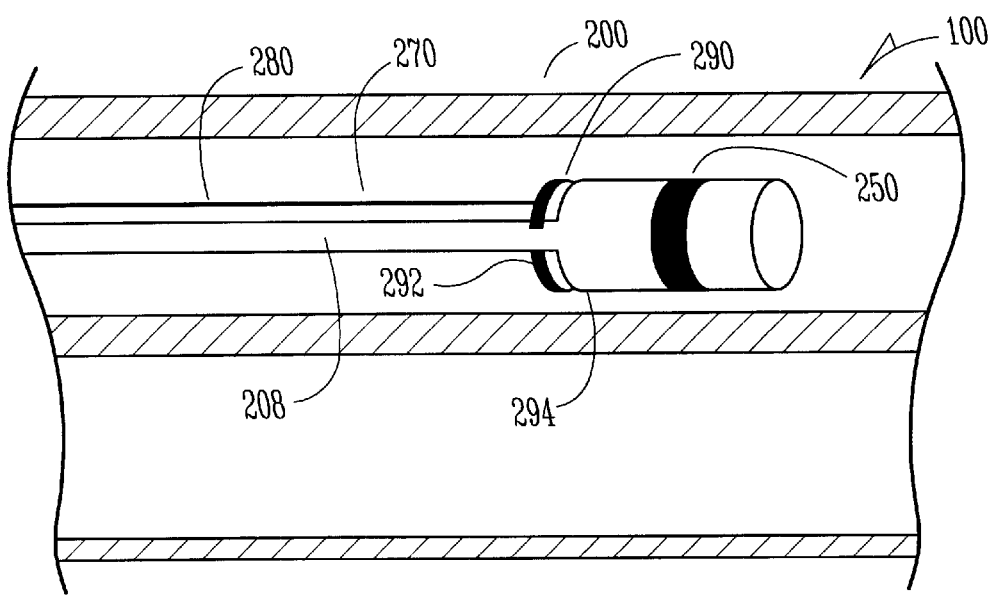
FIG. 5 shows a view of a segment of the system, where portions of the catheter have been removed to show detail.

FIG. 5 shows an exemplary embodiment of a pushing stylet 270 engaged with a lead without a stylet lumen. The pushing stylet 270 includes a push wire 280 and a head 290, where the push wire 280 is coupled to the head 290. The head 290 further includes a notched portion 292 that allows for the head 290 to at least partially surround the distal portion of the lead (in this example the second lead 208) where the lead has a shoulder 294 that is used at least partially to engage the pushing stylet 270. The push wire 280 has sufficient stiffness to allow for the pushing stylet 270 to advance the lead through the lumen of the catheter 200.

Referring again to FIG. 3, once the first and second leads have been implanted into the desired location of the heart, the elongate catheter is removed from the heart at 370. In one embodiment, the catheter is removed by holding or securing the proximal ends of the first and second leads and pulling the catheter towards the proximal ends of the leads. In one embodiment, once the distal ends of the leads pass into the lumens, the catheter is pulled until the catheter is removed from both the first and second leads. In one embodiment, the wall of each lumen is coated with a lubricious coating which is adapted to allow the leads to move easily through the lumen without disrupting the positioning of the leads within the heart. In an alternative embodiment, the leads are stabilized within the lumens of the catheter by positioning a wire against the distal end of the leads as the proximal ends pass into the lumen of catheter. The wires are then used to stabilize the leads (e.g., hold the leads in their implanted locations) as the catheter is passed over the leads.

In an alternative embodiment, removing the elongate catheter from the heart includes passing the catheter around the first and second cardiac leads 204 and 208. In one embodiment, this is accomplished with a splitable catheter, where the proximal end of the catheter is split into two or more segments and torn down the length of the catheter as it is removed from the patient to allow the catheter to be removed from the implanted cardiac leads.

Figure 6:
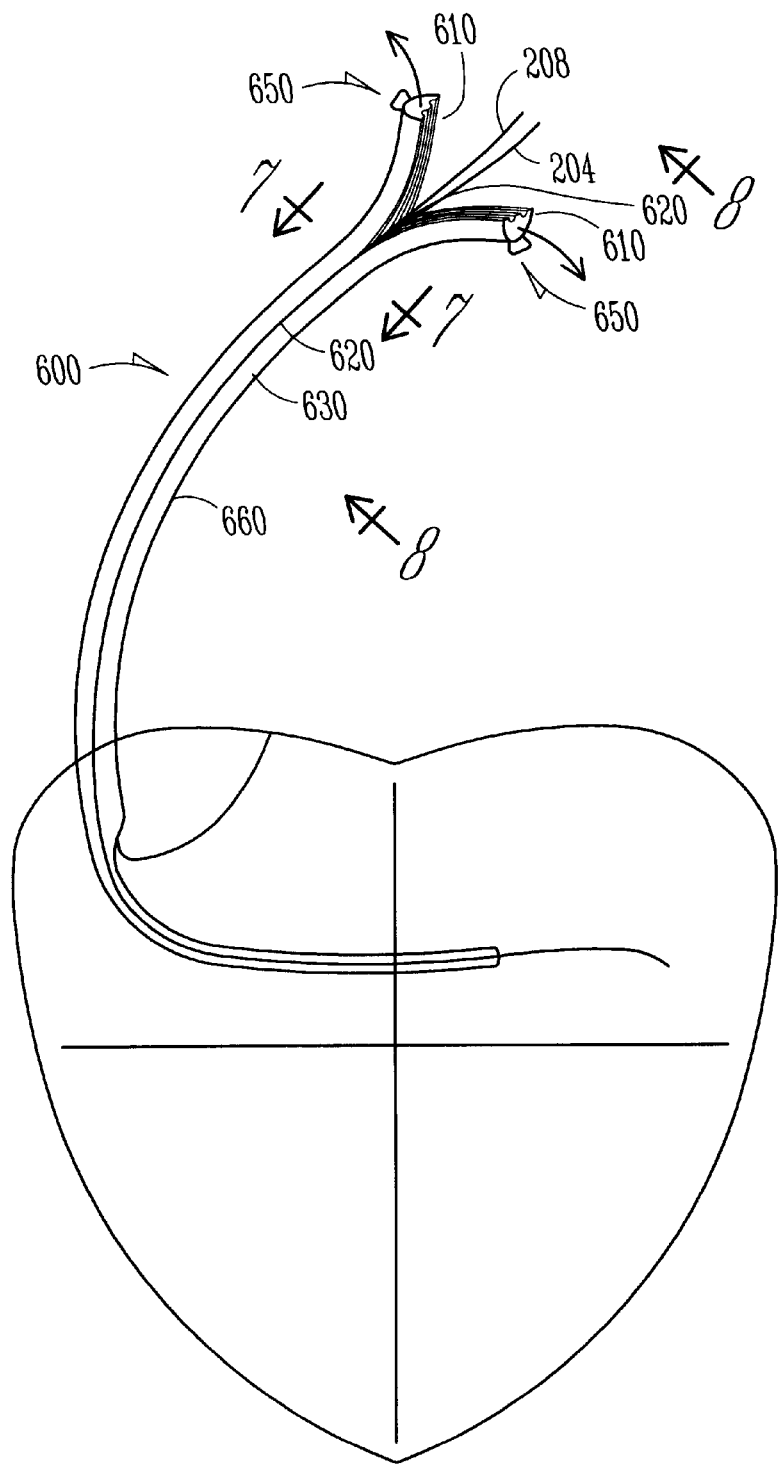
FIG. 6 shows a perspective view of an exemplary embodiment of a system partially implanted in a heart from which segments have been removed to show detail.

FIG. 6 shows an exemplary embodiment of a catheter 600 that is adapted to split into two or more segments 610 so as to allow the catheter to pass around the first and second cardiac leads 204 and 208. In one embodiment, the segments 610 of the splitable catheter 600 are defined by sections 620 of the catheter body 630, where the sections 620 are weaker relative to the remainder of the catheter body 630 and the segments 610 are adapted to separate from each other along the sections 620. In one embodiment, the sections 620 are weakened by longitudinally slitting the catheter body 630 at least partially through the thickness of the catheter body 630. Alternatively, the sections 620 are formed by weakening the material of the catheter body 630 by either removing or disrupting the material along the sections 620. In one embodiment, material is removed as the catheter body 630 is perforated along the sections 620.

Additionally, catheter 600 further includes a tab 650 positioned on each of the segments 610. The tab 650 is adapted to allow a person using the catheter 600 to more easily grip the segments 610 and to tear the catheter 600 along the sections 620. In one embodiment, the tab 650 on each of the segments 610 is located at the proximal end of the catheter body 630, where the tab 650 extends from proximal end to allow for the tab 650 to be gripped. In an additional embodiment, the tab 650 is a portion of the catheter body 630 that extends from a peripheral surface 660 of the catheter 600.

Figure 7:
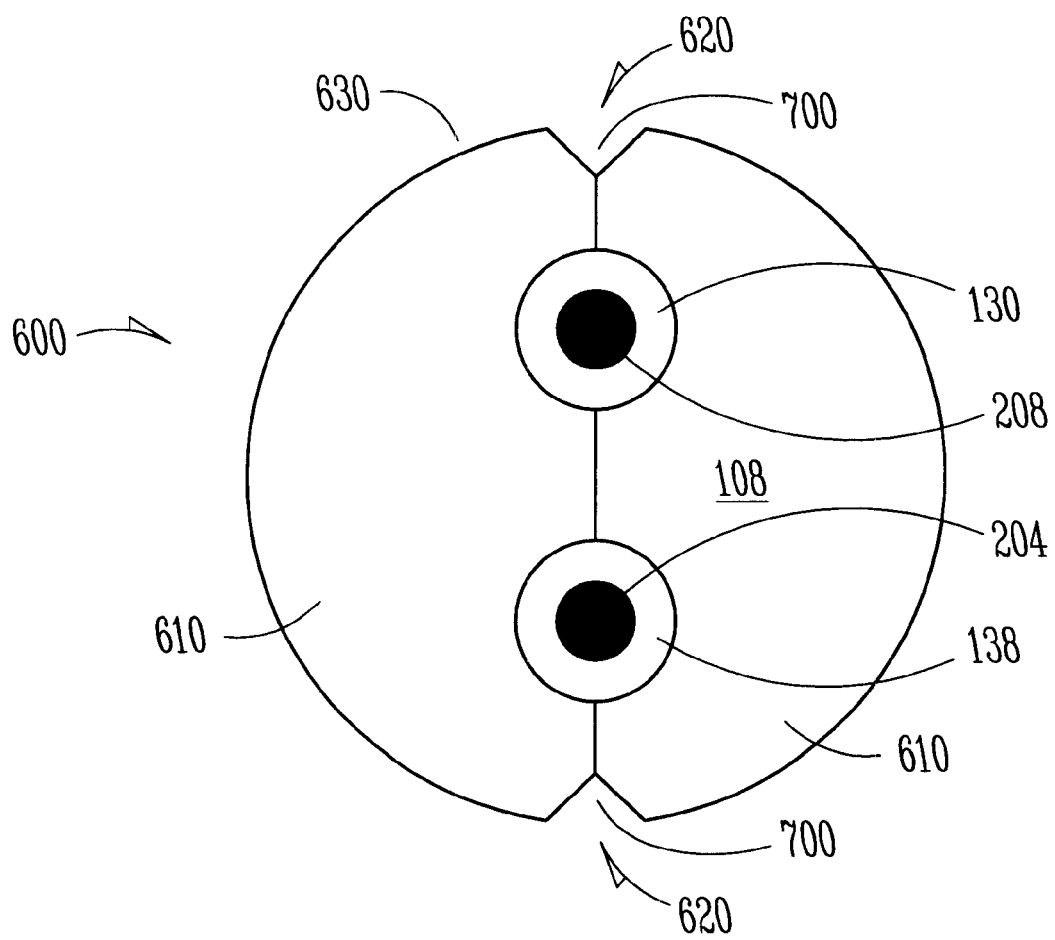
FIG. 7 shows a perspective view of a segment of the system of FIG. 6 taken along the lines 7—7.

FIG. 7 shows an alternative embodiment of the catheter 600, where material is removed from the catheter body 630 along the sections 620 so as to create a channel 700 as the area of weakness. The example of the channel 700 shown in FIG. 7 is a schematic of the proximal end 108 of the lead 600.

Figure 8:
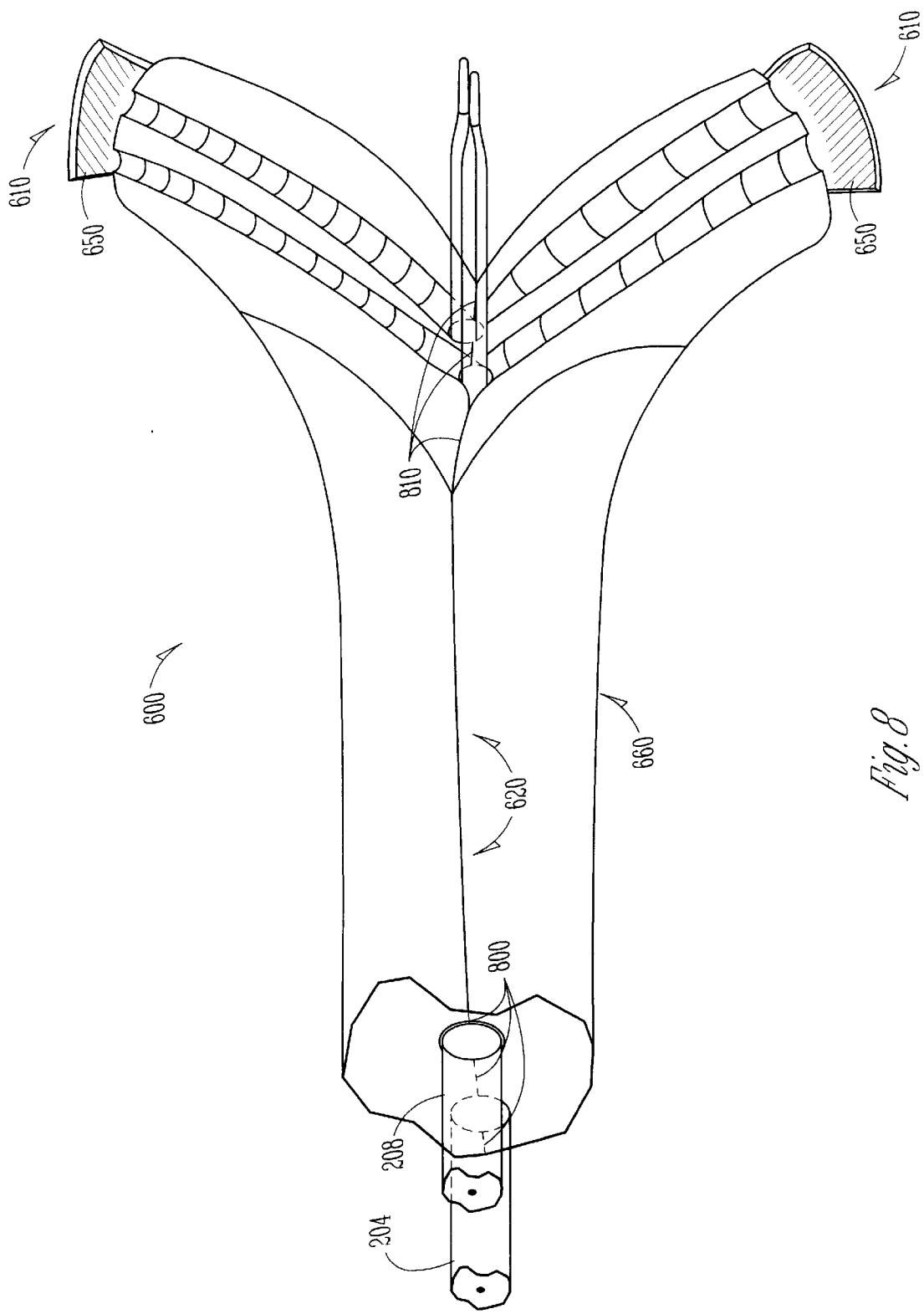
FIG. 8 shows a perspective view of a segment of the system of FIG. 6 taken along the lines 8—8.

FIG. 8 is an exemplary embodiment of the catheter 600 taken along the lines 8—8 in FIG. 6. FIG. 8 shows an embodiment in which the body of the catheter 600 has slits 800, where the slits create compose the sections 620. In one embodiment, the slits are sufficiently deep with respect to the thickness of the body of the catheter to allow a tear 810 to form between adjacent slits 800. Once torn, the segments 610 peel away from the first cardiac lead 204 and the second cardiac lead 208. This aspect of the catheter is important, as being able to peel the catheter away from the cardiac leads is accomplished rapidly and with fewer persons as compared to a catheter that is not adapted to tear or peel away from the implanted cardiac leads.

Figure 9:
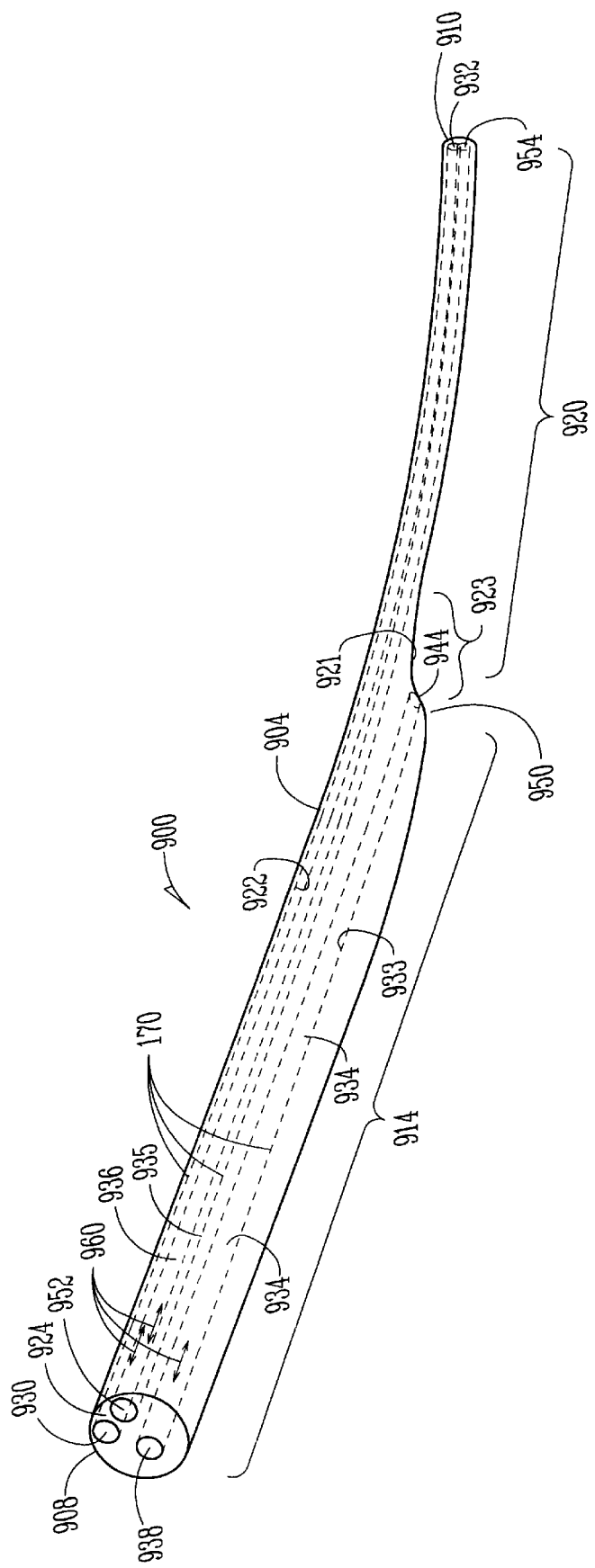
FIG. 9 shows a view of an exemplary embodiment of a catheter.

FIG. 9 shows an exemplary embodiment of a catheter 900. The catheter 900 includes an elongate catheter body 904 having a proximal end 908 and a distal end 910. The elongate catheter body 904 includes a first section 914 and a second section 920, where there is a transition 921 in the cross-sectional shape of the catheter body 904 between the first and second sections 914 and 920. In one embodiment, the transition 921 is a taper 923 having a circular cross-sectional shape from the first section 914 to the second section 920. The elongate catheter body 904 also includes a first wall 922 which defines a first lumen 924. The first lumen extends through the first section 914 and the second section 920. The first lumen 924 further includes a first inlet 930 at the proximal end 108 and a first outlet 932 at the distal end 910, where the first lumen 924 is adapted to receive and pass a cardiac lead.

The elongate catheter body 904 further includes a second wall 933 that defines a second lumen 934 and a third wall 935 that defines a third lumen 936. The second lumen 934 extends through the first section 914 between a second inlet 938 at the proximal end 908 to a second outlet 944 in the first section. In one embodiment, the second outlet 944 is located between the proximal end 908 and the distal end 910. The third lumen 936 extends through the first section 914 and the second section 920 between a third inlet 952 at the proximal end 908 to a third outlet 954 at the distal end 910. In an alternative embodiment, the third outlet 954 is positioned between the proximal end 908 and the distal end 910 of the catheter 900. As with the first lumen 924, the second lumen 934 and the third lumen 936 are also each adapted to receive and pass a cardiac lead.

The first lumen 924, the second lumen 934 and the third lumen 936 each have a longitudinal axis 960 which is separate from and parallel to each other, so that each lumen is spaced apart and separate from each other by the elongate catheter body 904 (i.e., the elongate catheter body 904 defines and separates each lumen). In one embodiment, the longitudinal axis 960 of the first lumen 924, the second lumen 934 and the third lumen 936 are eccentric with respect to each other (i.e., the longitudinal axis 960 of the first lumen 924, the second lumen 934 and the third lumen 936 do not have a common center with respect to each other). The first lumen 924 and the third lumen 936 also have a third lumen length that is greater than the second lumen length of the second lumen 934, where the first and third lumens 924 and 936 have approximately the same length.

In the exemplary embodiment of FIG. 9 there is shown a change in the size of the catheter body 904 at approximately 950. In one embodiment, the change in the catheter body 904 is the taper 923 which makes the transition between the first section 914 and the second section 920 of the catheter body 904. The second outlet 944 is located on the catheter body 904 along the tapered region 923. The transition also provides the second section 920 with a smaller profile than the first section 914, as previously discussed for FIG. 1.

The first lumen 924, the second lumen 934 and the third lumen 936 are each adapted to receive and pass a cardiac lead. In one embodiment, the first lumen diameter of the first lumen 924, the second lumen diameter of the second lumen 934 and the third lumen diameter of the third lumen 936 are each of a size sufficient to receive and pass a cardiac lead (i.e., to allow the cardiac lead to move completely through the lumen). In one embodiment, lumens are adapted to receive and pass cardiac leads having diameters in the range of approximately 0.5 millimeters to 2 millimeters.

The first lumen 924, the second lumen 934 and the third lumen 936 are each adapted to receive and pass a cardiac lead. In one embodiment, the diameter of each of the first lumen 924, second lumen 934 and the third lumen 936 is of a size sufficient to receive and pass a cardiac lead (i.e., to allow the cardiac lead to move completely through the lumen). In one embodiment, lumens 924, 934 and 936 are adapted to receive and pass cardiac leads having diameters in the range of approximately 0.5 millimeters to 2 millimeters.

In one embodiment, the catheter body 904 is constructed of an extruded thermopolymer. For example, the catheter body 904 is constructed of polyetheramide or other biocompatible polymer or co-polymers. In addition, the first wall 922, the second wall 933 and the third wall 935 of the catheter body 904 include a lubricious coating 170, which reduces the coefficient of friction between the cardiac lead and the catheter body 904. In one embodiment, the lubricous coating 170 is, for example, a hydrogel, cross-linked silicon, or other biocompatible lubricious coating materials applied by various means and manufacturing processes. In an additional embodiment, the catheter body 904 is made radiopaque. One reason for making the catheter body 904 radiopaque is to allow for the catheter 900 to be visualized as it is inserted into the patient.

Figure 10:
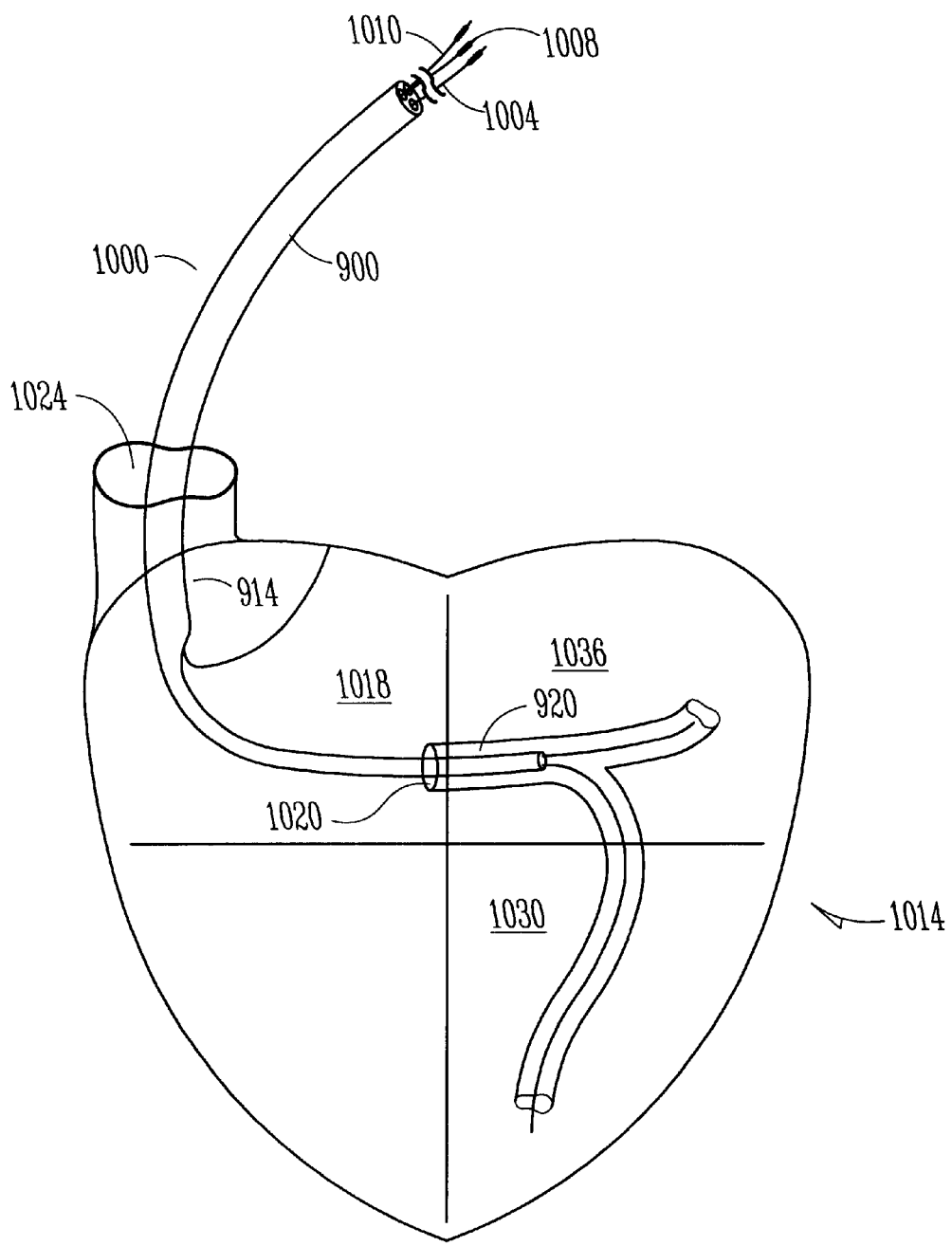
FIG. 10 shows a view of an exemplary embodiment of a system partially implanted in a heart from which segments have been removed to show detail.

FIG. 10 shows an exemplary embodiment of a system 1000. The system 1000 includes the catheter 900 as previously described, along with a first cardiac lead 1004, a second cardiac lead 1008 and a third cardiac lead 1010. The system 1000 is shown positioned in a heart 1014 with the first section 914 and the second section 920 positioned in the supraventricular region of the heart, where the second section 920 is positioned partially in the right atrium 1018 and partially the coronary sinus vein 1020 of the heart 1014 and the first section 914 positioned partially in the right atrium 1018 and partially in the superior vena cava 1024.

FIG. 10 shows the first cardiac lead 1004, the second cardiac lead 1008 and the third cardiac lead 1010 positioned at least partially within the first lumen, second lumen and third lumen, respectively. The lumens of the catheter have a diameter sufficient to allow the cardiac leads to be positioned within and to pass through the lumens. In one embodiment, each of the first cardiac lead 1004, the second cardiac lead 1008 and the third cardiac lead 1010 include a lumen adapted to receive a stylet, where the stylet is used in pushing the lead through the lumen of the catheter 900. Furthermore, the catheter 900 is adapted to receive and move over a guidewire positioned within the heart so as to implant the catheter 900 within the heart 1014, as previously described for catheter 100.

FIG. 10 also shows the distal portions of the first, second and third cardiac leads implanted within the heart 1014. The first cardiac lead 1004 is shown implanted into the coronary vasculature, where the distal end of the first cardiac lead 1004 is approximately positioned adjacent the left ventricle 1030 of the heart 1014. One or more electrodes on the first cardiac lead 1004 allow for at least one cardiac signal to be sensed and for electrical pulses to be delivered to the left ventricular 1030 region of the heart 1014. The second cardiac lead 1008 is shown implanted into the right atrium 1018, where the second cardiac lead 1008 includes one or more electrodes to allow for one or more cardiac signals to be sensed and for electrical pulses to be delivered to the heart 1014. Finally, the third cardiac lead 1010 is shown implanted into the coronary vasculature, where the distal end of the third cardiac lead 1010 is approximately positioned adjacent the left atrium 1036 of the heart 1014. One or more electrodes on the third cardiac lead 1010 allow for at least one cardiac signal to be sensed and for electrical pulses to be delivered to the left atrium 1036 region of the heart 1014.

Figure 11:
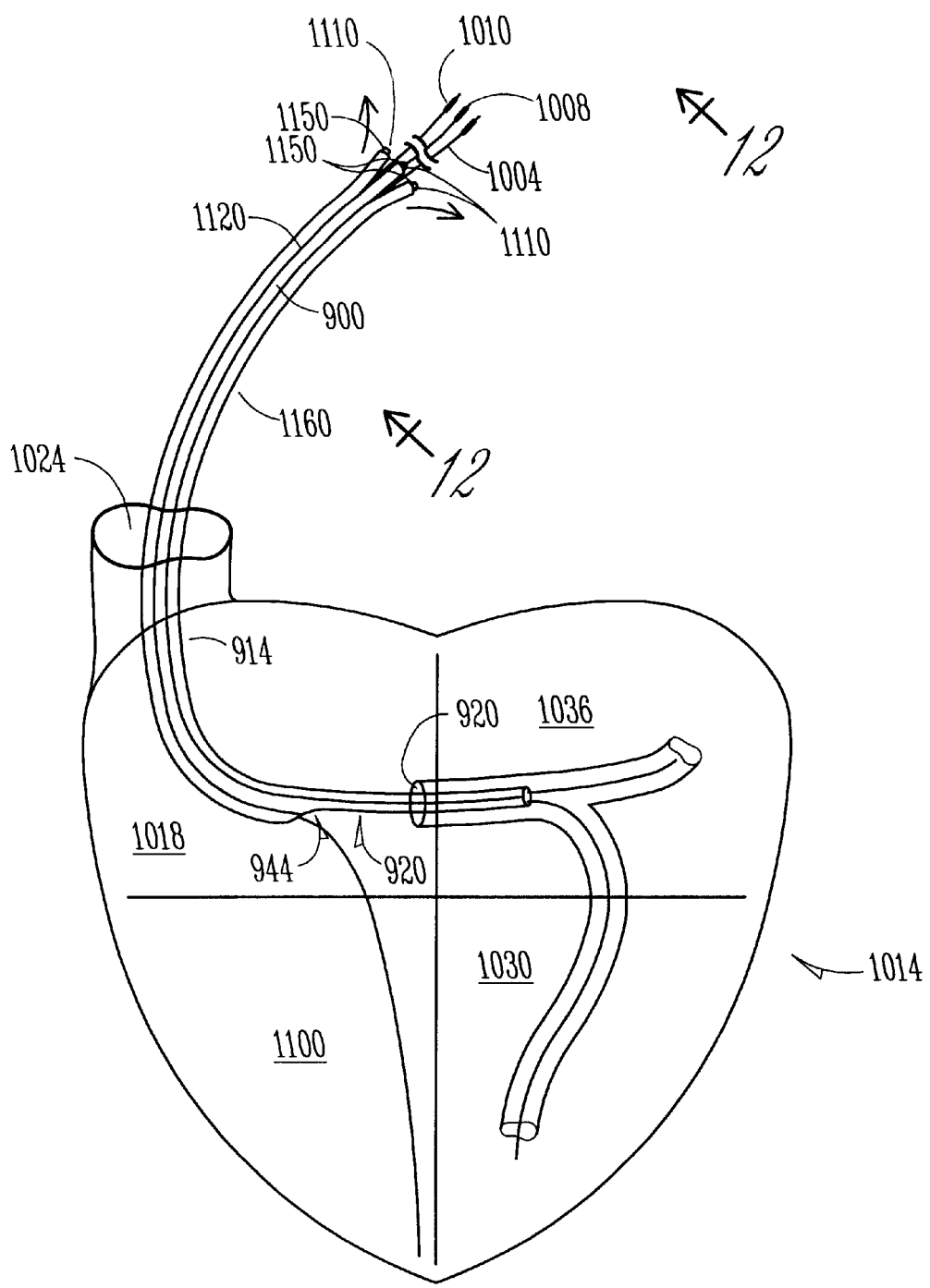
FIG. 11 shows a view of an exemplary embodiment of a system partially implanted in a heart from which segments have been removed to show detail.

FIG. 11 shows an additional exemplary embodiment of the system 1000 positioned within the heart 1014. The system 1000 is shown positioned in the heart 1014 with the first section 914 and the second section 920 positioned in the supraventricular region (1018 and 1036) of the heart 1014, where the second section 920 is positioned partially in the right atrium 1018 and partially the coronary sinus vein 1020 of the heart 1014 and the first section 914 positioned partially in the right atrium 1018 and partially in the superior vena cava 1024. In FIG. 11, the first and third cardiac leads 1004 and 1010 are positioned within the coronary veins, as previously described. The second cardiac lead 1008 is shown positioned with its distal end implanted in the right ventricle 1100 of the heart 1014.

The exemplary embodiment of FIG. 11 also shows the catheter 900 that is adapted to split into three or more segments 1110 so as to allow the catheter to pass around the first, second and third cardiac leads 1004, 1008 and 1010. In one embodiment, the segments 1110 of the splitable catheter 900 are defined by sections 1120 of the catheter body, where the sections 1120 are weaker relative to the remainder of the catheter body and the segments 1110 are adapted to separate from each other along the sections 1120. In one embodiment, the sections 1120 are weakened as previously described for the exemplary embodiments of FIGS. 6, 7 and 8.

Additionally, catheter 900 further includes a tab 1150 positioned on each of the segments 1110. The tab 1150 is adapted to allow a person using the catheter 900 to more easily grip the segments 1110 and to tear the catheter 900 along the sections 1120. In one embodiment, the tab 1150 on each of the segments 1110 is located at the proximal end of the catheter body, where the tab 1150 extends from proximal end to allow for the tab 1150 to be gripped. In an additional embodiment, the tab 1150 is a portion of the catheter body that extends from a peripheral surface 1160 of the catheter 900.

Figure 12:
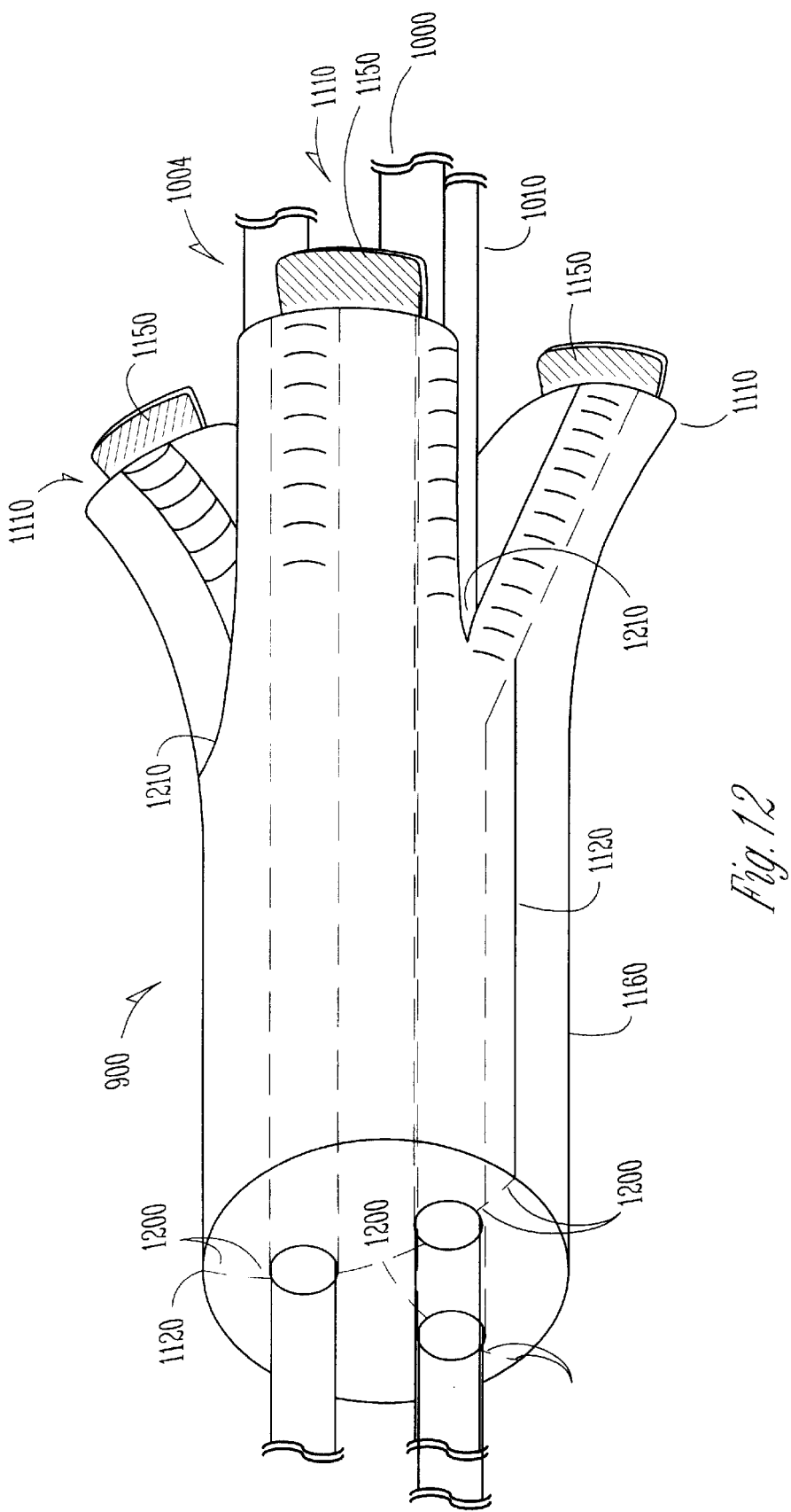
FIG. 12 shows a perspective view of a segment of the system of FIG. 9 taken along the lines 12—12.

FIG. 12 is an exemplary embodiment of the catheter 900 taken along the lines 12—12 in FIG. 11. FIG. 12 shows an embodiment in which the body of the catheter 900 has slits 1200, where the slits create compose the sections 1120. In one embodiment, the slits 1200 are sufficiently deep with respect to the thickness of the body of the catheter 900 so as to allow a tear 1210 to form between adjacent slits 1200. Once torn, the segments 1120 peel away from the first, second and third cardiac leads 1004, 1008 and 1010. This aspect of the catheter 900 is important as being able to peel the catheter 900 away from the cardiac leads is accomplished rapidly and with fewer persons as compared to a catheter that is not adapted to tear or peel-away from the implanted cardiac leads. For example, the peel-away catheter could be removed from the leads by a single person.

In addition to a catheter having three lumens which are adapted for delivering cardiac leads, it is also possible to have catheters having four or more lumens adapted for the same purpose. Furthermore, outlets for the four or more lumens are placed at any combination of positions between the proximal and distal ends of the catheter.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

I claim:
1. A catheter comprising:
  an elongate catheter body having a proximal end and a distal end, where the elongate catheter body includes a first section, a second section and a tapered region between the second section and the first section, the first section extending between the tapered region and the distal end and the second section extending between the proximal end and the tapered region, the tapered region positioned between the proximal and the distal ends of the elongate catheter body;

a first lumen adapted to pass a cardiac lead, the first lumen extending between a first inlet at the proximal end of the catheter body to a first outlet at the distal end of the catheter body;

a second lumen adapted to pass a cardiac lead, the second lumen extending through the second section of the elongate catheter body between a second inlet at the proximal end of the elongate catheter body to a second outlet in the tapered region; and wherein the elongate catheter body is adapted to separate into two or more segments.

2. The catheter of claim 1, wherein the first lumen and the second lumen each have a longitudinal axis that are parallel to each other and are spaced apart and separated by a portion of the elongate catheter body from each other.

3. The catheter of claim 1, wherein the longitudinal axis of the first lumen and the second lumen are eccentric with respect to each other.

4. The catheter of claim 1, wherein the first lumen has a first lumen length and the second lumen has a second lumen length, where the first lumen length is greater than the second lumen length.

5. The catheter of claim 1, wherein the first lumen has a first lumen diameter and the second lumen has a second lumen diameter, where the first and second lumen diameters are each adapted to receive and pass the cardiac lead having a lead diameter of approximately 0.5 millimeters to 2 millimeters.

6. The catheter of claim 1, wherein the first lumen is defined by a first wall and the second lumen is defined by a second wall, where the first or second wall each have a lubricious coating.

7. The catheter of claim 1, wherein the catheter body is made radiopaque.

8. The catheter of claim 1, wherein the two or more segments of the elongate catheter body are defined by slits extending longitudinally along the catheter body.

9. The catheter of claim 1, wherein the first lumen is defined by a first wall and the second lumen is defined by a second wall, where the first and second wall each have a lubricious coating.

10. The catheter of claim 1, including a third lumen adapted to pass a cardiac lead, the third lumen extending through the first section between a third inlet at the proximal end to a third outlet at the distal end of the catheter body.

11. The catheter of claim 10, wherein the first lumen, the second lumen and the third lumen each have a longitudinal axis which is separated from and parallel to each other.

12. The catheter of claim 11, wherein the longitudinal axis of the first lumen, the second lumen and the third lumen are eccentric with respect to each other.

13. The catheter of claim 10, wherein the third lumen has a diameter adapted to receive and pass a lead having a diameter in the range of approximately 0.5 millimeters to 2 millimeters.

14. The catheter of claim 10, wherein the third lumen is defined by a third wall, where the third wall has a lubricious coating.

15. A catheter comprising:

an elongate catheter body having a proximal end and a distal end, where the elongate catheter body includes a first section, a second section and a tapered region between the second section and the first section, the first section extending between the tapered region and the distal end and the second section extending between the proximal end and the tapered region, the tapered region positioned between the proximal and the distal ends of the elongate catheter body;

a first lumen adapted to pass a cardiac lead, the first lumen extending between a first inlet at the proximal end of the catheter body to a first outlet at the distal end of the catheter body;

a second lumen adapted to pass a cardiac lead, the second lumen extending through the second section of the elongate catheter body between a second inlet at the proximal end of the elongate catheter body to a second outlet in the tapered region; and wherein the elongate catheter body is adapted to separate into three or more segments.

16. The catheter of claim 15, wherein the three or more segments of the elongate catheter body are defined by slits extending longitudinally along the catheter body.

17. A system comprising:

a catheter, the catheter including:

an elongate catheter body having a proximal end and a distal end, where the elongate catheter body includes a first section, a second section and a tapered region between the second section and the first section, the first section extending between the tapered region and the distal end and the second section extending between the proximal end and the tapered region, the tapered region positioned between the proximal and the distal ends of the elongate catheter body;

a first lumen adapted to pass a cardiac lead, the first lumen extending through the first section of the elongate catheter body between a first inlet at the proximal end of the catheter body to a first outlet at the distal end of the catheter body; and a second lumen adapted to pass a cardiac lead, the second lumen extending through the second section of the elongate catheter body between a second inlet at the proximal end of the elongate catheter body to a second outlet in the tapered region;

a first cardiac lead, where at least a portion of the first cardiac lead is located in and passes through the first lumen of the elongate catheter body; and a second cardiac lead, where at least a portion of the second cardiac lead is located in and passes through the second lumen of the elongate catheter body.

18. The system of claim 17, wherein the first lumen is defined by a first wall and the second lumen is defined by a second wall, where the first and second wall each have a lubricious coating.

19. The system of claim 17, wherein the elongate catheter body is made radiopaque.

20. The system of claim 17, wherein the elongate catheter body is adapted to separate into two or more segments.

21. The system of claim 20, wherein the two or more segments of the elongate catheter body are defined by slits extending longitudinally along the catheter body.

22. The system of claim 17, including a third lumen extending through the first section between a third inlet at the proximal end to a third outlet at the distal end of the catheter body; and a third cardiac lead, where at least a portion of the third cardiac lead is located in and passes through the third lumen of the elongate catheter body.

23. The system of claim 22, wherein the third lumen is defined by a third wall, where the third wall has a lubricious coating.

24. The system of claim 22, wherein the elongate catheter body is adapted to separate into three or more segments.

25. The system of claim 24, wherein the three or more segments of the elongate catheter body are defined by slits extending longitudinally along the catheter body.

26. The system of claim 22, wherein the first cardiac lead and the second cardiac lead and the third cardiac lead each include a lumen adapted to receive a stylet.

27. A method comprising:

positioning a guidewire within a heart;

inserting an elongate catheter into the heart over the guidewire, where the elongate catheter includes a first lumen and a second lumen;

removing the guidewire from the heart;

implanting a first cardiac lead into the heart through the first lumen;

implanting a second cardiac lead into the heart through the second lumen; and removing the elongate catheter from the heart.

28. The method of claim 27, wherein implanting the first cardiac lead includes:

inserting the first cardiac lead into the first lumen of the elongate catheter; and advancing the first cardiac lead with a stylet through the first lumen.

29. The method of claim 27, wherein implanting the second cardiac lead includes:

inserting the second cardiac lead into the second lumen of the elongate catheter; and advancing the second cardiac lead with a stylet through the second lumen.

30. The method of claim 27, wherein inserting the elongate catheter includes visualizing the elongate catheter with a venogram.

31. The method of claim 27, wherein removing the elongate catheter from the heart includes separating the elongate catheter into at least two segments as the catheter is removed from the heart.

32. The method of claim 31, wherein removing the elongate catheter includes passing the at least two segments around the first cardiac lead and the second cardiac lead.

33. The method of claim 27, wherein implanting the first cardiac lead includes implanting the first cardiac lead into a right ventricle of the heart.

34. The method of claim 27, wherein implanting the first cardiac lead includes implanting the first cardiac lead into a right atrium of the heart.

35. The method of claim 27, wherein implanting the second cardiac lead includes implanting the second cardiac lead into a supraventricular region of the heart.

36. The method of claim 27, wherein implanting the second cardiac lead includes implanting the second cardiac lead adjacent a left ventricle of the heart.

* * * * *